(12) United States Patent
Franz

(10) Patent No.: US 11,116,719 B2
(45) Date of Patent: *Sep. 14, 2021

(54) METHODS OF TREATING MENIERE'S DISEASE

(71) Applicant: Burkhard Karl-Heinz Gunther Franz, Melbourne (AU)

(72) Inventor: Burkhard Karl-Heinz Gunther Franz, Melbourne (AU)

( * ) Notice: Subject to any disclaimer, the term of this patent is extended or adjusted under 35 U.S.C. 154(b) by 0 days.

This patent is subject to a terminal disclaimer.

(21) Appl. No.: 16/518,078

(22) Filed: Jul. 22, 2019

(65) Prior Publication Data
US 2020/0016070 A1    Jan. 16, 2020

Related U.S. Application Data

(63) Continuation-in-part of application No. PCT/AU2018/000041, filed on Mar. 22, 2018.

(30) Foreign Application Priority Data

Mar. 22, 2017   (AU) ................................ 2017901006

(51) Int. Cl.
*A61K 9/00* (2006.01)
*A61P 27/16* (2006.01)
*A61B 5/00* (2006.01)
*A61K 31/4402* (2006.01)

(52) U.S. Cl.
CPC ............ *A61K 9/0043* (2013.01); *A61B 5/407* (2013.01); *A61K 31/4402* (2013.01); *A61P 27/16* (2018.01)

(58) Field of Classification Search
CPC .............. A61K 9/0043; A61K 31/4402; A61B 5/407; A61P 27/16
See application file for complete search history.

(56) References Cited

U.S. PATENT DOCUMENTS

| 8,642,631 | B2* | 2/2014 | Anderson | A61P 1/08 514/357 |
| 2011/0166190 | A1* | 7/2011 | Anderson | A61P 1/08 514/357 |
| 2015/0359738 | A1* | 12/2015 | Mulvahill | A61K 31/137 424/450 |
| 2018/0214432 | A1* | 8/2018 | Wraight | A61K 9/0073 |

OTHER PUBLICATIONS

England et al. "Nasal pH Measurement: a reliable and repeatable parameter," Clin Otolaryngol Allied Sci 1999, abstract.*
Labuguen ("Initial Evaluation of Vertigo" in American Family Physician, 2006.*
Melville Da Cruz ("Meniere's disease, a stepwise approach" in Medicine Today, 2014, 15(3), 18-26).*
Franz et al.,Measuring dynamic Eustachian tube function using tympanometry in a pressure chamber:the effect of nasal betahistine application, The Journal of Laryngology & Otology, 2019, pp. 1-8.
Lacour et al., Betahistine in the treatment of Meniere's disease, Neuropsychiatric Disease and Treatment, 2007, pp. 429-440, vol. 3, Issue 4.

\* cited by examiner

*Primary Examiner* — Blessing M Fubara
(74) *Attorney, Agent, or Firm* — Benjamin Aaron Adler

(57) ABSTRACT

Methods of treating a human patient suffering from Eustachian tube malfunctions are provided. A nasal spray or pharmaceutical composition containing a therapeutically effective amount of betahistine is administered to the patient. The nasal spray or pharmaceutical composition has particular applicability to alleviate the symptoms of Meniere's disease in persons suffering from abnormal Eustachian tube function, but also has an applicability to beneficially improve vascular oxygenation of the inner ear.

9 Claims, 2 Drawing Sheets

METHODS OF TREATING MENIERE'S DISEASE

BACKGROUND OF THE INVENTION

Technical Field

The present invention relates to compounds, compositions and method used for treatment of a sub-population of Meniere's disease. In particular, this invention concerns the improvement of a person's Eustachian tube function and improvement of vascular oxygenation of the inner ear by use of betahistine in sub-population exemplified by secondary Meniere's disease.

Description of the Related Art

Ménière's disease (MD) is a balance disorder characterized by a triad of symptoms rather than a given cause: fluctuating hearing loss, attacks of vertigo and tinnitus. There are multiple forms of Meniere's disease with many different causes and balance disorders affect a large proportion of the world's population. The etiology of this disorder is still unclear and successful pharmaceutical treatments are wide ranging and generally lacking.

In addition to the classical symptom triad, accessory symptoms are invariably present: fullness or blockage in the ear suggesting a Eustachian tube dysfunction, neck/jaw discomfort suggesting a functional disorder of the cervical spine and/or temporomandibular joints, and mydriasis reflecting an activated cervical sympathetic nervous system.

An important morphological and diagnostic feature in idiopathic and secondary Ménière's disease is the endolymphatic hydrops, an expansion of the endolymph fluid compartment of the inner ear. The expansion of the endolymph fluid compartment can be demonstrated by electrocochleography, an averaging examination technique that measures the electrical response of the inner ear to clicks. Typically, it will show a raised SP/AP ratio (Summating Potential/Action Potential).

As Meniere's disease can have a variety of causes, it should not be surprising that different causes would therefore respond to different treatments. Syphilis and an acoustic neuroma are two possible causes of Meniere's disease. As Syphilis is caused by a bacterial infection, its resulting Meniere's disease would be treated with penicillin. Meniere's disease caused by acoustic neuroma is treated by surgery to remove the tumor.

No medication has been approved by the FDA to prevent or treat Meniere's disease. At present an extremely large number of treatments are being used to treat Meniere's disease. Some of the treatments include: (1) changes to diet such as restricting intake of salt; (2) medications including thiazide diuretics; (3) streptomycin therapy; (4) Physiotherapy with attention to the upper cervical spine and temporomandibular joints; (5) nutritional supplements such as ginger, lipoflavinoids; and (6) surgical procedures that cut the balance nerve or drain fluid from the inner ear.

All of the foregoing treatments fall short of being completely successful. For example, streptomycin therapy while effective in vertigo control, may have an ototoxic effect after repeated treatments. The ability of invasive surgery such as endolymphatic sac surgery, to produce an intended result appears positive, however such procedures can be highly stressful for elderly patients, and in addition can be frustrating when drainage is prevented by fibrosis of the endolymphatic duct.

A further treatment of Meniere's disease is the Meniett device. This treatment requires insertion of a tympanostomy tube, which qualifies as a surgical treatment, and whereby the Meniett device delivers pulses of pressure to the inner ear via the tympanostomy tube. A general understanding of why this device works is not well understood although some patients receive symptomatic relief when the device is used on a daily basis.

While there is some anecdotal evidence of betahistine assisting persons with Meniere's disease, there has been no properly based study reported which supports such use. WO2009/143572 by the present applicant (Franz et al.) suggests a method for treating Eustachian tube dysfunction including the step of topically applying to a patient an effective amount of betahistine. Betahistine is a histamine-like drug believed to improve blood supply to the inner ear and it has a possible effect of reducing sensitivity of the vestibular system. The testing detailed in WO2009/143572 was limited to rat models, and results in the rat model studies indicating a potential for use of betahistine to treat humans suffering from Eustachian tube dysfunction.

The same rat model studies were described by the applicant in Franz et al. ("Topical application of betahistine improves Eustachian tube function in an animal model" ACTA OTO-LARYNGOLOGICA, 2011, vol. 131, no. 11, pp. 1155-1159). This study showed that, in the rat model, Eustachian tube function was improved following application of betahistine. This indicated potential for use of betahistine to treat disorders involving Eustachian tube dysfunction in humans.

Following the above findings, a clinical trial was proposed. The proposed trial is the subject of a publication entitled OTIFEX THERAPEUTICS, "A phase Ib, Randomized, Placebo-Controlled, Double Blind Study to Evaluate Two Concentrations of Betahistine Dihydrochloride Spray Administered as a Single Intranasal Dose in Adult Male and Female Volunteers with Eustachian Tube Dysfunction". However, such a trial was not commenced and did not proceed as parallel trials had found, contrary to rat model studies, administration of betahistine to humans with Eustachian tube dysfunction gave no greater result than a placebo. Consequently, the Food and Drug Administration (FDA) in the USA removed betahistine from a list of acceptable treatments for Meniere's disease.

The present applicant reconfigured the proposed trial above but not to test volunteers with Eustachian tube dysfunction. The volunteers were selected for the study without consideration as to whether or not they had a Eustachian tube dysfunction. The reconfigured trial was set up to test the effect of betahistine on eustachian tube function using tympanometry on a cohort of "normal" volunteers. The trial specifically excluded any participant who had symptoms of Meniere's disease. This exclusion is shown at item 20 of the Exclusion Criteria listed in the aforementioned publication. The reconfigured trial found that, at best, betahistine had no effect, and in cases of higher dosages the effect was adverse as Eustachian tube function became worse (Franz et al.: Eustachian Tube Function Using Tympanometry in a Pressure Chamber: The Effect of Nasal Betahistine Application. Journal Laryngol Otol, Jun. 24, 2019, online). This finding supports conventional knowledge that betahistine has either no effect or indeed makes any Eustachian tube function worse. At the conclusion of the reconfigured trial, it was found that some of the volunteers had mild Eustachian tube dysfunction, which was not improved with betahistine.

In view of the above, it is desirable to have a treatment of Meniere's disease that addresses or ameliorates at least one or more of the prior art deficiencies or at least provides a practical variation to avert one or more of the prior art deficiencies. It is to be understood that, if any prior art information is referred to herein, such reference does not constitute an admission that the information forms part of the common general knowledge in the art, in Australia or any other country.

SUMMARY OF THE INVENTION

The invention has been developed primarily for use in treatment of secondary Meniere's disease and has particular applicability to alleviate the symptoms of Meniere's disease in persons suffering from abnormal Eustachian tube function associated with an activated cervical sympathetic nervous system, and will be described hereinafter with reference to this application. However, it is appreciated that the invention is not limited to this particular field of use.

According to a first aspect of the present invention, there is provided a method of treating a human patient suffering from secondary Meniere's disease having an activated cervical sympathetic nervous system and a mild Eustachian tube dysfunction, by administering an effective dose of betahistine or an acceptable pharmaceutical salt.

The present invention has surprisingly found that betahistine has a desirable effect on a sub-population of people presenting with secondary Meniere's disease. By administration of betahistine in patients with an activated cervical sympathetic nervous system, which resulted in a mild Eustachian tube dysfunction through neurogenic inflammation, applicant has found that betahistine does not cause a further aggravation of Eustachian tube function as expected, but to the contrary resulted in facilitation of Eustachian tube function. This is clearly contrary to conventional knowledge in this field and therefore a surprising and useful effect in treating the select sub-population presenting with secondary Meniere's disease.

Preferably the method of the invention includes the step of testing the patient's cervical sympathetic nervous system for determining status of patient's sympathetic nervous system. The step of testing the patient's cervical sympathetic nervous system can be performed by manipulating the patient's neck. This step identifies a patient having an activated cervical sympathetic nervous system, which resulted in a mild Eustachian tube dysfunction. A patient identified as having the above symptoms represents a select sub-population of secondary Meniere's disease which presents with an elevated SP/AP ratio which can be subsequently normalized by treatment with betahistine.

In one embodiment the activity of a patient's sympathetic nervous system can be examined by the step of steadying and maintaining the patient's head in a forward position while the patient is seated in a chair or the like and turning the chair.

Preferably, betahistine or a pharmaceutically acceptable salt is administered to a patient determined as suffering from the identified secondary Meniere's disease, in an oral form. Preferably, the oral dosage form of betahistine is administered initially in an amount of 16 mg three time daily. The effect of administration of betahistine in the subpopulation of patient's identified as suffering from secondary Meniere's disease can be monitored by ECochG and dosages adjusted depending on the SP/AP ratios determined from the ECochG results.

The betahistine treatment regimen can be continued for a predetermined period and successful outcomes assessed on the effect on stabilization and/or normalization of SP/AP amplitude ratio as determined by audiological methods such as electrocochleography (ECochG).

Preferably the effective dose of betahistine or an acceptable pharmaceutical salt is administered topically. In one aspect the invention provides a method of treating a human patient suffering from Eustachian tube malfunction comprising administering to the patient a nasal spray comprising an efficacious amount of betahistine or an acceptable pharmaceutical salt.

In another aspect the invention provides a method of improving vascular oxygenation of an inner ear of a patient comprising administering to the patient a nasal spray comprising an efficacious amount of betahistine or an acceptable pharmaceutical salt.

In another aspect the invention provides a method of a two way improvement of inner ear oxygenation of a patient, via the middle ear and vascular system, comprising administering to said patient a nasal spray comprising an efficacious amount of betahistine or an acceptable pharmaceutical salt.

In another aspect the invention provides a method of treating a human patient suffering from Meniere's disease due to Eustachian tube malfunction where an imbalance exists of the autonomic nervous system whereby the sympathetic has been activated, the method comprising administering to the patient a nasal spray comprising an efficacious amount of betahistine or an acceptable pharmaceutical salt.

In another aspect the invention provides a method of improving vascular oxygenation of an inner ear of a patient suffering from Meniere's disease and having an imbalance of the autonomic nervous system whereby the sympathetic has been activated, the method comprising administering to the patient a nasal spray comprising an efficacious amount of betahistine or an acceptable pharmaceutical salt.

Preferably the efficacious amount is within the range 0.2 to 5.0 mg of betahistine or an acceptable pharmaceutical salt in solution sprayed into each nostril. More preferably the efficacious amount is within the range 0.5 to 2.0 mg of betahistine or an acceptable pharmaceutical salt in solution sprayed into each nostril. Preferably the efficacious amount is sprayed into each nostril as a solution within the range 4 to 8 mg/ml of betahistine or an acceptable pharmaceutical salt in solution adjusted to pH 5.5.

In a further related aspect of the invention there is provided use of betahistine or an acceptable pharmaceutical salt for the manufacture of a medicament for the treatment of secondary Meniere's disease.

In yet a further related aspect of the invention there is provided a pharmaceutical composition containing betahistine or an acceptable pharmaceutical salt and pharmaceutically acceptable carrier when used for the treatment of secondary Meniere's disease.

The present invention has found that a select sub-population of human patients suffering from secondary Meniere's disease comprising an activated cervical sympathetic nervous system and a mild Eustachian tube dysfunction can be successfully treated with betahistine, that is, it is a particular subgroup identified by the applicant that responds to betahistine. In each case where a patient's Eustachian tube was mildly dysfunctional and the sympathetic nervous system was found to be activated. Applicant has found that patients suffering from secondary MD, show improved treatment outcomes by consistently responding to betahistine medication, contrary to expectation that there would be no improvement or indeed exacerbation of the symptoms.

Therefore in an even further related aspect of the present invention there is provided betahistine or an acceptable pharmaceutical salt when used for the treatment of a subpopulation of human patients suffering from secondary Meniere's disease comprising an activated cervical sympathetic nervous system and a mild Eustachian tube dysfunction.

BRIEF DESCRIPTION OF THE DRAWINGS

Notwithstanding any other forms which may fall within the scope of the present invention, preferred embodiments of the invention will now be described, by way of example only, with reference to the accompanying drawings in which.

DETAILED DESCRIPTION OF THE INVENTION

Figure 1:
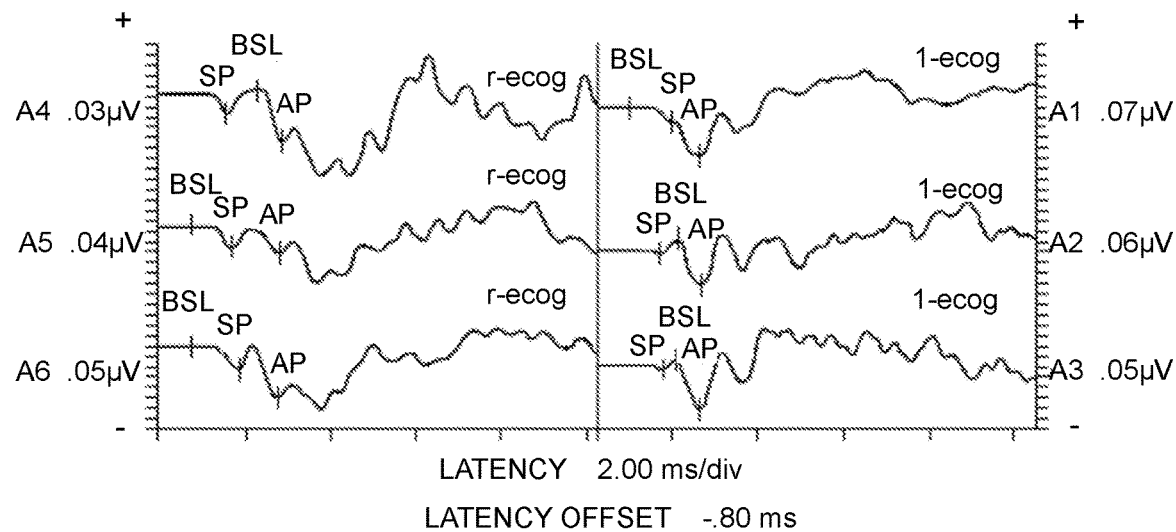
FIG. 1 is a bio-logic evoked potential report based on an ECochG conducted on a human patient before treatment with betahistine.

The present invention provides compositions and methods for treatment of Meniere's disease. In one aspect, the method comprises administering to an individual diagnosed with Meniere's disease a composition comprising an efficacious amount of betahistine or an acceptable pharmaceutical salt, wherein the individual is also diagnosed with a secondary form of Meniere's disease having an activated sympathetic nervous system. Betahistine or an acceptable pharmaceutical salt is preferably administered topically via the nasal route in a spray form in an amount of between 0.2 to 5 mg in each nostril.

Studies have found that around 15-20% of the oxygenation of the inner ear depends on the supply of oxygen via the middle ear. This suggests that good middle ear ventilation is crucial for inner ear function.

It has been found that for some patients with Meniere's disease showed improvement of Eustachian tube function while under betahistine medication. Similarly, the insertion of a middle ear ventilation tube, which practically eliminates Eustachian tube dysfunction, can alleviate the symptoms of Meniere's disease. All patients in this category had an enlarged pupil on the side of the affected ear and showed an immediate further enlargement of the pupil when the body was turned against a steadied head, reflecting a functional disorder of the cervical spine. Cervical spine treatment by physiotherapy has shown to lessen Meniere's disease symptoms in these instances, resulting in some people claiming that Meniere's disease is nothing but a neck problem.

While betahistine might have no effect on Eustachian tube function in normal subjects, or might even worsen Eustachian tube function, the effect is different when an imbalance exists of the autonomic nervous system, particularly when the cervical sympathetic is activated as can happen in functional disorders of the upper cervical spine and temporomandibular joints (Upper Quarter Syndrome). In this situation an activated cervical sympathetic can cause via an axon reflex a Eustachian tube dysfunction through neurogenic inflammation. The effect of betahistine in this situation is reversed resulting in improvement of Eustachian tube function. It is achieved by altering the blood supply to the Eustachian tube and alteration of gland secretion.

An explanation for the unexpected beneficial effect of the present invention derives from the multi-step realization that Meniere's disease is, in many instances caused or exacerbated by reduced oxygenation of the inner ear, and that improving ventilation of the middle ear could sufficiently improve oxygenation of the inner ear, and that administering betahistine in a nasal spray could alter gland secretion sufficiently to facilitate Eustachian tube opening to allow sufficiently improved ventilation of the middle ear, which would in turn improve oxygenation of the inner ear and thus alleviate the symptoms of Meniere's disease.

In one aspect of the invention betahistine or an acceptable pharmaceutical salt can be administered via a nasal spray although other modes of delivery are acceptable. However, topical application has a number of advantages, among them, higher concentrations can be used than through oral administration (betahistine has been shown to be nontoxic in high concentrations). Topical application to the nasopharynx is directed to where action is required. Through nasal application betahistine quickly enters the blood stream through turbinate absorption without incurring the highly variable destruction which occurs in the stomach when administered orally. Improved oxygenation of the inner ear is achieved via the vascular system and improved middle ear ventilation.

A preferred administration rate is in the range 0.5 to 2.0 mg betahistine, as 4 to 8 mg/ml betahistine in solution, with an adjusted pH of 5.5, sprayed into each nostril three times daily. This can be achieved by spraying into each nostril one or two puffs, each of round 150 to 200 μl, of betahistine in solution at a concentration of 4 to 8 mg/ml. As betahistine is considered as non-toxic when administered at much higher levels, the invention envisages the use of much higher dosages of betahistine to fall within the scope of this invention, even though the increase may contribute to change of efficacy.

Definitions/Terms

In general, terms used in the claims and the specification are intended to be construed as having the plain meaning understood by a person of ordinary skill in the art. Certain terms are defined below to provide additional clarity. In case of conflict between the plain meaning and the provided definitions, the provided definitions are to be used. Terms used in the claims and specification are defined as set forth below unless otherwise specified or by their usage throughout this disclosure.

Methods are known in the art for determining therapeutically effective doses or pharmaceutically effective doses for therapeutic and prophylactic purposes for the disclosed pharmaceutical compositions or the disclosed drug combinations, whether or not formulated in the same composition. For therapeutic purposes, the term "therapeutically effective amount" or "therapeutically effective dose" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "therapeutically effective amount" refers to that amount of each active compound or pharmaceutical agent, alone or in combination, that treats or inhibits in a subject the onset or progression of a disorder as being sought by a researcher, medical doctor or other clinician.

The term "Meniere's disease" refers to a disease or disorder, progressive or not, of the inner ear. The "classic" presentation of Meniere's disease is vertigo, hearing loss, and tinnitus. Herein, the term Meniere's disease is not to be constrained to be interpreted as a condition or disorder which is limited to only those which have all three of the aforementioned symptoms. Rather, Meniere's disease is taken to be a disorder which is diagnosed as described in Example 1.

The term "endolymphatic hydrops" refers to the swelling of the endolymphatic compartment due to an accumulation of endolymphatic fluid in the inner ear.

"Electrocochleography" (ECochG) is an auditory evoked potential test that is used to assess the inner ear functions. ECochG is a well-known diagnostic test of endolymphatic hydrops.

ECochG response is composed of three components cochlear microphonics (CMs), Summating Potentials (SP) and Action Potentials (AP). SP is a direct current response generated by hair cells of the organ of Corti and a reflection of the displacement-time pattern of the cochlear partition. AP is the summed response of numerous, at times thousands, of ANFs firing synchronously.

An important parameter in the analysis of the ECochG response is measuring the amplitude of SP and AP to derive an SP/AP amplitude ratio. It is known that an elevated SP/AP ratio is a common finding in cases of Endolymphatic Hydrops (ELH)/Meniere's disease (MD).

The term "pharmaceutically acceptable salt" refers to non-toxic pharmaceutically acceptable salts (Ref. International J. Pharm, 1986, 33, 201-217; J. Pharm. Sci., 1997 (January), 66, 1, 1). Other salts well known to those in the art may, however, be useful in the preparation of compounds according to this disclosure or of their pharmaceutically acceptable salts. Representative organic or inorganic acids include, but are not limited to, hydrochloric, hydrobromic, hydroiodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid.

Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The term "composition" is intended to encompass a product comprising the specified ingredients in the specified amounts, as well as any product which results, directly or indirectly, from combinations of the specified ingredients in the specified amounts.

Dosages

For the methods for the treatment of secondary MD and/or endolymphatic hydrops described herein, the dosage form will contain a pharmaceutically acceptable carrier containing up to about 16 mg; preferably between from about 0.2 mg to about 5 mg; particularly from about 0.5 mg to about 2 mg; of betahistine or pharmaceutically acceptable salt, and may be constituted into any form suitable for the mode of administration selected. The dosages, however, may be varied depending upon the requirement of the subjects, the severity of the condition being treated and the compound being employed. The use of either daily administration or post-periodic dosing may be employed.

Compounds disclosed herein can be administered in topical, oral, intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Formulations

To prepare the pharmaceutical compositions disclosed herein, one or more compounds disclosed herein or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in The Handbook of Pharmaceutical Excipients, published by the American Pharmaceutical Association and the Pharmaceutical Society of Great Britain.

EXAMPLES

Example 1: Clinical Treatment of Meniere's Disease Patients

Introduction

Meniere's disease (MD) is defined as a triad of episodic vertigo, hearing loss and tinnitus. Aural pressure or fullness is often reported and most auditory and vestibular symptoms fluctuate in frequency and intensity. Endolymphatic hydrops is a swelling of the endolymphatic compartment of the inner ear and has been directly linked to Meniere's disease. Most Meniere's disease patients are medically managed using a low-salt diet and/or a thiazide diuretic with limited success. After an acute phase where vertigo is the most common feature, the chronic phase emerges, where hearing loss and tinnitus become the most common features, although disequilibrium is often reported.

Meniere's Disease Criteria

Diagnostic Criteria for Meniere's Disease

Possible Meniere's disease;

Episodic vertigo of the Meniere's type without documented hearing loss, or

Sensorineural hearing loss, fluctuating or fixed, with disequilibrium but without definitive episodes other causes excluded;

Probable Meniere's disease;

One definitive episode of vertigo;

Audiometrically documented hearing loss on at least one occasion;

Tinnitus or aural fullness in the treated ear; and

Other causes excluded.

Study Design

Patients, aged 19-70 years, have undergone baseline testing to determine SP/AP amplitude ratio using ECochG in Meniere's disease patients before the start of study treatment. The effect on SP/AP amplitude ratio was evaluated after a predetermined period of treatment with betahistine or a pharmaceutically acceptable salt.

Description of Treatment

Patients were seated in a swivel chair and the chair rotated while the patient's head was stabilized. Effect of rotational movement was observed and pupil enlargement a determinant of secondary Meniere's disease.

Dosing Levels:

Dose levels included 16 mg of betahistine three time daily for predetermined period. 8 mg dose twice daily thereafter for a second predetermined period.

Dosing Regimen:

Patient studies comprise a range of dosing regimens including tablets, powders, sprays. In present studies unless otherwise stated each dose was administered in a tablet form in the morning taken after food.

Dosage Form:

Route of Administration can include oral and topical delivery. In the present studies unless otherwise stated route of administration was oral delivery.

Study Procedures

Audiometric Testing:

Audiological evaluations were performed at specified intervals to evaluate the efficacy of Tests performed by physician or qualified audiologist. ECochG was performed at specified intervals by a physician specialist. Patient reported outcomes by self-administered questionnaire included the VSS (Yardley et al. 2004) and the TFI (Meikle et al. 2011). These were scored by study personnel.

Patient Study

A male patient of 39 years of age presented with a history of intermittent attacks of vertigo associated with a gradual deterioration of his hearing and tinnitus in the right ear. Patient indicated he was involved in a car accident many years before but was uncertain whether he suffered a whiplash injury. An otological assessment of the patient showed bilaterally intact and transparent ear drums. A Weber tuning fork test was directed into the left ear. The Rinne tuning fork test was positive bilaterally. There was no spontaneous or provoked nystagmus under Frenzel glasses. A Hallpike manoeuvre was unremarkable, not suggesting benign paroxysmal positioning vertigo. Performing an Unterberger stepping test, the patient slightly turned to the right. Conduct of a Halmagyi impulse test was unremarkable.

Palpation of the neck revealed some myoclonus of upper neck muscles and head movement was slightly restricted to both sides. On palpation there was tenderness over the occipital nerves. Observation of pupil size under Frenzel glasses revealed a slightly enlarged pupil on the right side.

Patient Electrocochleogram SP/AP Ratio—Before Treatment

An audiological assessment revealed a mild low frequency sensorineural hearing loss in the right ear and a mild high frequency sensorineural hearing loss in the left ear. Tympanometry showed mildly reduced middle ear pressure in the right ear. Tympanogram in the left ear was normal. Brainstem audiometry showed normal tracings and latencies in both ears not suggesting retrocochlear pathology.

Referring to FIG. 1, there is shown an electrocochleogram bio-logic evoked potential report before treatment. Results detailed in Tables 1 and 2 (see below) show the SP/AP ratio for left and right ear of the patient before commencement of treatment. Results of the ECochG determine the left ear within normal ratio (average ratio of 28.6%) however an elevated SP/AP ratio (average ratio of 57%) in the right ear reflecting condition of endolymphatic hydrops.

TABLE 1 before treatment inter-amplitudes

| | INTERAMPLITUDES (uV) | | | | |
|---|---|---|---|---|---|
| I III | III V | I V | SP BSL | AP BSL | SP/AP |
| A1 | | | +.10 | +.34 | .30 |
| A2 | | | +.09 | +.26 | .34 |
| A3 | | | +.05 | +.24 | .22 |
| A4 | | | +.08 | +.16 | .50 |
| A5 | | | +.09 | +.12 | .72 |
| A6 | | | +.12 | +.23 | .49 |

TABLE 2

Average SP/AP ratio before treatment

| Left Ear SP/AP Ratio | Right Ear SP/AP Ratio |
|---|---|
| 30 | 50 |
| 34 | 72 |
| 22 | 49 |
| Average Ratio of 28.6% | Average Ratio of 57% |

The history and audiological findings particularly the shape of the right audiogram with a low frequency sensorineural hearing loss, tympanometry in the right ear showing reduced middle ear ventilation, the presence of endolymphatic hydrops in the right ear and the immediate enlargement of the right pupil during the shoulder turn test were consistent with a diagnosis of secondary Ménière's disease associated with a mild Eustachian tube dysfunction and an activated sympathetic, the latter most likely linked to a functional disorder of the cervical spine.

Determination of Activation Status of the Sympathetic Nervous System

The patient was seated on a swivel chair, the patient's head steadied in a forward position and patient turned on a swivel chair. During this procedure pupils were observed under Frenzel glasses. Almost immediately upon swivel, the patient's right pupil enlarged indicating activation of the sympathetic nervous system and functional disorder of the cervical spine. Examination of the jaw was unremarkable.

Treatment with Betahistine

Patient was started on oral dosage form of betahistine 16 mg three times daily (tds) for two weeks and reduced to 8 mg once daily thereafter for two months.

Patient Electrocochleogram SP/AP Ratio—After Treatment

Figure 2:
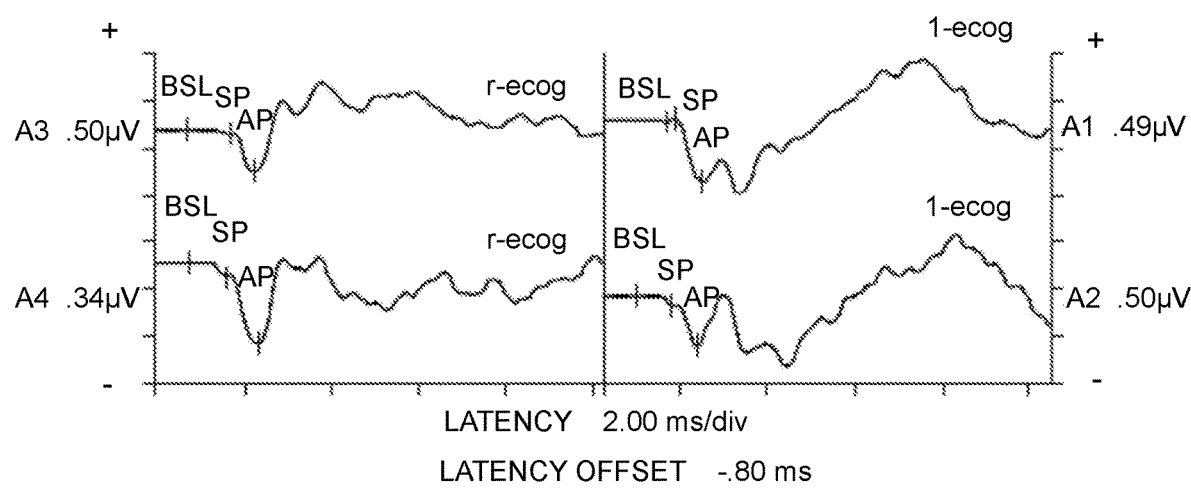
FIG. 2 is a bio-logic evoked potential report based on an ECochG conducted on a human patient of FIG. 1 after treatment with betahistine.

A review at two months into the treatment showed that symptoms had improved significantly and repeat electrocochleograms (see FIG. 2) had returned to normal levels consistent with a good treatment outcome. Further management such as insertion of a middle ear ventilation tube was not necessary. Table 3 and 4 (below) shows significant decrease in average SP/AP ratio. In particular decrease in patient's right ear from average SP/AP ratio of 57% to 16%.

TABLE 3

After Treatment with oral Serc

| | INTERAMPLITUDES (uV) | | | | |
|---|---|---|---|---|---|
| I III | III V | I V | SP BSL | AP BSL | SP/AP |
| A1 | | | +.05 | +.68 | .07 |
| A2 | | | +.13 | +.53 | .25 |

TABLE 3-continued

After Treatment with oral Serc

| | INTERAMPLITUDES (uV) | | | | |
|---|---|---|---|---|---|
| I III | III V | I V | SP BSL | AP BSL | SP/AP |
| A3 | | | +.04 | +.44 | .09 |
| A4 | | | +.10 | +.57 | .18 |

TABLE 4

Average SP/AP ratio after treatment

| Left Ear SP/AP Ratio | Right Ear SP/AP Ratio |
|---|---|
| 7 | 9 |
| 25 | 18 |
| Average Ratio of 16% | Average Ratio of 13.5% |

Patient Study

A male patient of 69 years old presented with concern regarding his hearing and head movement related dizziness. Pure tone audiometry testing showed a mild high frequency sensorineural hearing loss in the left ear and a mild low and high frequency sensorineural hearing loss on the right. Bone conduction asymmetry was noted at 500 to 1000 Hz in the poorer right ear and at 4 and 6 kHz in the poorer left ear.

Figure 3:
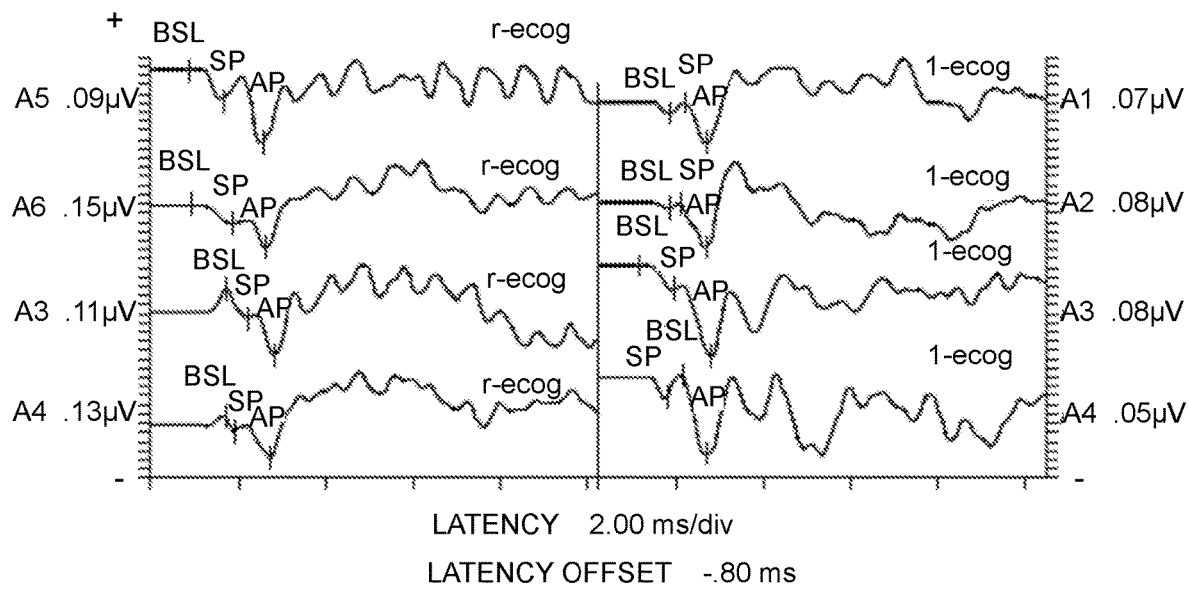
FIG. 3 is a bio-logic evoked potential report based on an ECochG conducted on a human patient before treatment with betahistine.

Speech recognition was consistent with the audiogram. Impedance audiometry revealed type A tympanogram of normal middle ear compliance in the left and a Type C tympanogram of reduced middle ear pressure and consistent with Eustachian tube dysfunction in the right. Ipsilateral acoustic reflexes were elicited at normal limits in the left ear at 1 and 2 kHz only. ECochG test was performed on the patient before and after treatment. FIG. 3 shows a bio-logic evoked potential electrocochleogram report with data analyses in Tables 5 and 6 below.

TABLE 5 before treatment inter-amplitudes

| | INTERAMPLITUDES (uV) | | | | |
|---|---|---|---|---|---|
| I III | III V | I V | SP BSL | AP BSL | SP/AP |
| A1 | | | +.08 | +.30 | .26 |
| A2 | | | +.07 | +.39 | .18 |
| A3 | | | +.21 | +.75 | .28 |
| A4 | | | +.12 | +.40 | .30 |
| A5 | | | +.25 | +.68 | .37 |
| A6 | | | +.30 | +.68 | .44 |
| A7 | | | +.33 | +.76 | .44 |
| A8 | | | +.20 | +.54 | .37 |

TABLE 6

Average SP/AP ratio before treatment

| Left Ear SP/AP Ratio | Right Ear SP/AP Ratio |
|---|---|
| 26 | 37 |
| 18 | 44 |
| 28 | 44 |
| 30 | 37 |
| Average Ratio of 25.5% | Average Ratio of 40.5% |

Determination of Activation Status of the Sympathetic Nervous System

The patient was seated on a swivel chair, the patient's head steadied in a forward position and patient turned on a swivel chair. During this procedure pupils were observed under Frenzel glasses. Almost immediately upon swivel, the patient's right pupil enlarged indicating activation of the sympathetic nervous system and functional disorder of the cervical spine.

Treatment with Betahistine

Patient was started on oral dosage form of betahistine 16 mg three times daily (tds) for two weeks and reduced to 8 mg once daily thereafter for two months.

Patient Electrocochleogram SP/AP Ratio—After Treatment

Figure 4:
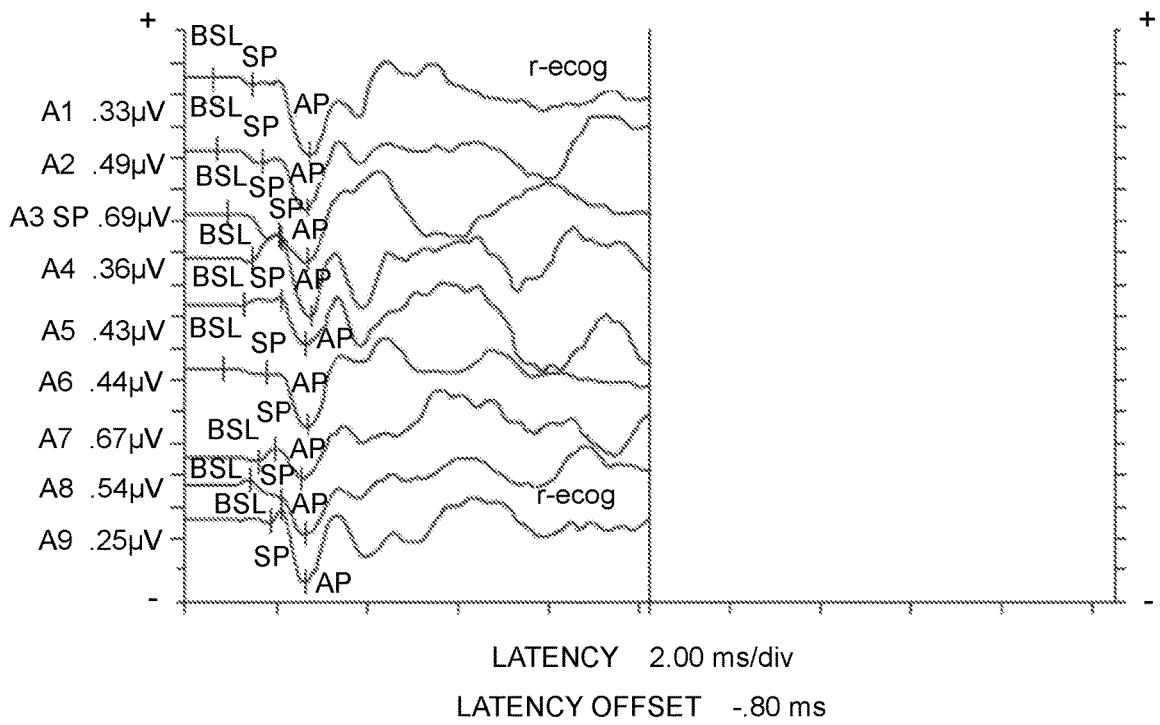
FIG. 4 is a bio-logic evoked potential report based on an ECochG conducted on a human patient of FIG. 3 after treatment with betahistine.

A review at two months showed symptoms had improved significantly and repeat electrocochleograms (see FIG. 4) had returned to normal levels consistent with a good treatment outcome.

Table 7, 8 and 9 (below) shows significant decrease in average SP/AP ratio. In particular decrease in patient's right ear from average SP/AP ratio of 4.5% to 22%. And patient's left ear SP/AP ratio decreased from 25.5% to 9.5%.

TABLE 7

After Treatment with oral Serc (Right ear)

| | INTERAMPLITUDES (uV) | | | | |
|---|---|---|---|---|---|
| I III | III V | I V | SP BSL | AP BSL | SP/AP |
| A1 | | | +.09 | +.80 | .12 |
| A2 | | | +.19 | +.93 | .20 |
| A3 | | | +.63 | +.10 | .57 |
| A4 | | | +.31 | +.93 | .33 |
| A5 | | | +.15 | +.67 | .22 |
| A6 | | | +.07 | +.84 | .08 |
| A7 | | | +.27 | +.65 | .41 |
| A8 | | | +.33 | +.92 | .36 |
| A9 | | | +.13 | +.63 | .20 |

TABLE 8

After Treatment with oral Serc (Left ear)

| | INTERAMPLITUDES (uV) | | | | |
|---|---|---|---|---|---|
| I III | III V | I V | SP BSL | AP BSL | SP/AP |
| A1 | | | +.20 | +2.55 | .08 |
| A2 | | | +.10 | +1.96 | .05 |
| A3 | | | +.61 | +2.99 | .20 |
| A4 | | | +.38 | +2.91 | .13 |
| A5 | | | +.44 | +2.72 | .16 |
| A6 | | | +.35 | +2.93 | .12 |
| A7 | | | +.45 | +1.93 | .23 |
| A8 | | | +.21 | +2.04 | .10 |
| A9 | | | +.32 | +2.07 | .15 |

TABLE 9

Average SP/AP ratio after treatment

| Left Ear SP/AP Ratio | Right Ear SP/AP Ratio |
|---|---|
| 8 | 12 |
| .5 | 20 |
| 10 | 36 |
| 5 | 20 |
| Average Ratio of 9.5% | Average Ratio of 22% |

Applicant has found that treating endolymphatic hydrops by addressing a Eustachian tube dysfunction that resulted from an activated sympathetic nervous system, i.e. in patients suffering from secondary MD, invariably improved treatment outcomes by consistently responding to betahistine medication.

In all cases, the treatment provided by betahistine, normalized an elevated SP/AP ratio that otherwise previously indicated endolymphatic hydrops.

The applicant has found that the present invention shows successful treatment can be achieved in patients having this form of secondary Meniere's disease, and that it is particularly this subgroup that responds to betahistine. In each case where a patient's Eustachian tube was mildly dysfunctional and the sympathetic nervous system was found to be activated, an enlarged pupil was observed that resulted in an immediate further enlargement by the activation step.

This discovery and treatment is contrary to all existing convention and represents a departure from and advance over the existing art in the field. The treatment regimen is extremely beneficial to a sub-population of patients suffering from secondary Meniere's disease.

Whilst the above description includes the preferred embodiments of the invention it is to be understood that many variations, alterations and/or additions may be introduced into the constructions and arrangements of parts previously described without departing from the essential features or the spirit or ambit of the invention.

It will be also understood that where the word "comprise", and variations such as "comprises" and "comprising" are used in this specification, unless the context requires otherwise such use is intended to imply the inclusion of a stated feature or features, but is not to be taken as exclusive the presence of other feature or features.

The reference to any prior art in this specification is not, and should not be taken as, an acknowledgment or any form of suggestion that such prior art forms part of the common general knowledge.

What is claimed is:

1. A method of treating a human patient suffering from secondary Meniere's disease, the method comprising administering to the patient a composition comprising an efficacious amount of betahistine or an acceptable pharmaceutical salt thereof, wherein patients suffering from secondary Meniere's Disease present with specific characteristics comprising an activated cervical sympathetic nervous system with a mild eustachian tube (ET) dysfunction associated therewith, wherein the ET dysfunction upsets the inner ear resulting in endolymphatic hydrops whereby the hydrops causes Meniere's disease symptoms.

2. The method according to claim 1, wherein said efficacious amount is within the range 0.2 to 5.0 mg of the betahistine or the acceptable pharmaceutical salt thereof in a solution sprayed into each nostril.

3. The method according to claim 2, wherein said efficacious amount is within the range 0.5 to 2.0 mg of betahistine or the acceptable pharmaceutical salt in the solution sprayed into each nostril.

4. The method according to claim 2, wherein said solution sprayed into each nostril has a concentration of betahistine or the acceptable pharmaceutical salt within the range 4 to 8 mg/ml.

5. The method of claim 1, wherein the composition comprises the betahistine or an acceptable pharmaceutical salt thereof in solution at pH 5.5 and with a concentration within the range of 4.0 mg/ml to 8.0 mg/ml, said concentration sufficient to deliver an efficacious amount per dosage.

6. The method of claim 1, wherein the composition is a pharmaceutical composition further comprising a pharmaceutically acceptable carrier.

7. A method of treating a human patient suffering from secondary Meniere's disease comprising:
   determining a patient having an activated cervical sympathetic nervous system by detecting an enlarged pupil on the side of an affected ear; and
   administering an effective dose of betahistine or an acceptable pharmaceutical salt thereof, wherein patients suffering from secondary Meniere's disease present with specific characteristics comprising an activated cervical sympathetic nervous system having a mild eustachian tube (ET) dysfunction associated therewith, wherein the ET dysfunction upsets the inner ear resulting in endolymphatic hydrops whereby the hydrops causes Meniere's disease symptoms.

8. The method of claim 7, wherein determining a patient having an activated cervical sympathetic nervous system further comprises turning the patient's body against a steadied head and observing further enlargement of the enlarged pupil.

9. The method of claim 7, wherein the step of turning the patient's body against a steadied head is performed by the step of steadying and maintaining the patient's head in a forward position while the patient is seated in a chair or the like and turning the chair.

* * * * *